United States Patent
Zenker (10) Patent No.: US 11,684,406 B2
(45) Date of Patent: Jun. 27, 2023

(54) PLASMA TREATMENT DEVICE

(71) Applicant: Erbe Elektromedizin GmbH, Tuebingen (DE)

(72) Inventor: Matthias Zenker, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 553 days.

(21) Appl. No.: 16/703,174

(22) Filed: Dec. 4, 2019

(65) Prior Publication Data

US 2020/0179030 A1 Jun. 11, 2020

(30) Foreign Application Priority Data

Dec. 5, 2018 (EP) ..................................... 18210346

(51) Int. Cl.
*A61B 18/00* (2006.01)
*A61B 18/04* (2006.01)
*H05H 1/24* (2006.01)
*A61B 18/12* (2006.01)

(52) U.S. Cl.
CPC ............. *A61B 18/042* (2013.01); *H05H 1/24* (2013.01); *A61B 18/1206* (2013.01); *A61B 2018/00642* (2013.01); *A61B 2018/00982* (2013.01)

(58) Field of Classification Search
None
See application file for complete search history.

(56) References Cited

U.S. PATENT DOCUMENTS

| | | | |
|---|---|---|---|
| 6,210,410 B1 | 4/2001 | Farin et al. | |
| 7,066,933 B2 | 6/2006 | Hagg | |
| 8,575,843 B2 | 11/2013 | Moore et al. | |
| 2001/0034519 A1* | 10/2001 | Goble | A61B 18/042 606/41 |
| 2005/0177150 A1* | 8/2005 | Amoah | A61B 18/1206 606/45 |

(Continued)

FOREIGN PATENT DOCUMENTS

| | | |
|---|---|---|
| DE | 69632080 T2 | 2/2005 |
| EP | 1307154 B1 | 2/2005 |

(Continued)

OTHER PUBLICATIONS

European Search Report dated Jun. 5, 2019, in corresponding European Application No. 18210346.5 (8 pages).

(Continued)

*Primary Examiner* — Linda C Dvorak
*Assistant Examiner* — Nicholas S Borsch
(74) *Attorney, Agent, or Firm* — Fitch, Even, Tabin & Flannery LLP (57) ABSTRACT

The plasma sensor monitors parameters characterizing the condition of the plasma during the treatment phase and/or the change thereof in order to recognize a prefiguring or already occurred interruption of the plasma in this manner and to avoid this interruption and, in the ideal case, avoid this by already changing the voltage form previously. The mentioned mechanisms can be used by the control device (22) also during a pulse packet. The length of each pulse packet is adapted at each change of the voltage form according to their characteristics in order to guarantee a constant average power.

14 Claims, 4 Drawing Sheets

(56) References Cited

U.S. PATENT DOCUMENTS

| | | | |
|---|---|---|---|
| 2006/0189974 A1* | 8/2006 | Penny | A61B 18/042 606/41 |
| 2011/0077642 A1 | 3/2011 | Farin | |
| 2011/0101862 A1* | 5/2011 | Koo | H01J 37/32559 315/111.21 |
| 2011/0121735 A1 | 5/2011 | Penny | |
| 2012/0022522 A1* | 1/2012 | Suslov | A61B 18/1206 606/34 |
| 2012/0271304 A1* | 10/2012 | Werner | A61B 18/1233 606/45 |
| 2012/0283732 A1* | 11/2012 | Lam | A61B 17/00491 606/49 |
| 2013/0199540 A1* | 8/2013 | Buske | A61B 18/042 128/845 |
| 2019/0132937 A1* | 5/2019 | Eckert | H05H 1/2406 |

FOREIGN PATENT DOCUMENTS

| | | |
|---|---|---|
| EP | 2514380 A1 | 10/2012 |
| EP | 2231046 B1 | 3/2016 |
| GB | 2552452 A | 1/2018 |
| JP | 2014236993 A | 12/2014 |
| RU | 2245491 C2 | 1/2005 |
| RU | 2304934 C2 | 8/2007 |
| RU | 2456472 C2 | 7/2012 |
| RU | 149459 U1 | 1/2015 |
| WO | 1998/025530 A1 | 6/1998 |
| WO | 2002/011634 A1 | 2/2002 |
| WO | 2018/094159 A1 | 5/2018 |

OTHER PUBLICATIONS

India Patent Office, Office Action in corresponding Patent Application No. 201914048812, dated Oct. 21, 2022, 5 pages.

Federal Service for Intellectual Property (FIPS), Office Action dated Nov. 8, 2022 for Russian Patent Application No. 2019137999; 21 pages.

Japanese Patent Office; Notice of Reasons for Refusal for JP Patent Application No. 2019-218702 dated Apr. 17, 2023; 7 pages.

* cited by examiner

PLASMA TREATMENT DEVICE

RELATED APPLICATION(S)

This application claims the benefit of European Patent Application No. 18210346.5, filed Dec. 5, 2018, the contents of which is incorporated herein by reference as if fully rewritten herein.

TECHNICAL FIELD

The invention refers to a plasma treatment device with improved handling, particularly an argon plasma treatment device. The plasma treatment can be a coagulation, a devitalization, a vaporization or a separation of tissue. Also possible is a cold plasma treatment with the object of a disinfection or wound treatment, for example.

BACKGROUND

From DE 696 320 80 T2 an endoscopic argon plasma endoscope coagulator is known that comprises a flexible hose in the lumen of which an electrode is arranged. The electrode is approximately connected with a radio frequency generator via a conductor, wherein the radio frequency generator applies a radio frequency voltage to the electrode. The flexible probe is inserted into a lumen of an endoscope that comprises a lens at its distal end that forms part of a monitoring optic. The field of view of the lens is orientated, such that the location of treatment and thus the spark or plasma jet originating from the electrode is within the field of view of the operator.

The coagulation device of WO 98/25530 A1 is similarly configured.

EP 2 231 046 B1 refers to the voltage supply of such a plasma applicator that is to be inserted in a working channel of a flexible endoscope. The short duration of the ignition of a spark is considered as critical moment in this document, during which a current may flow having an undesired high amount. For remedy a resistor element is connected ahead of the electrode.

From DE 50 105 427 A1 a generator is known, wherein the provided power can be adjusted by modification of the voltage form, particularly the modulation of the pulse/pause ratio. The peak voltage and thus the intensity of a light arc or spark are kept constant.

From EP 1 307 154 B1 a generator with adjustable limitation of the effective power output is known, in which the pulse/pause ratio of the modulated radio frequency voltage is varied for power modulation.

Basically the treating person of the plasma treatment desires a reliable and immediate creation of a spark or a plasma at the activation. However, undesired effects of the plasma ignition and/or the electric current transmitted via the plasma shall be avoided or minimized. Such undesired effects are, e.g. the dazzling of the treating person, a too intense noise creation, a too intense, too fast or too extended thermal damage of the tissue, a puncture thereof, a too intense electro-magnetic interference or a combination thereof.

Therefrom the object is derived to provide a plasma treatment device with improved handling.

SUMMARY

The object is solved with a device for plasma treatment and/or a method as disclosed herein.

A generator is part of the inventive device, wherein the generator is configured to create a radio frequency alternating voltage (radio frequency voltage) in different adjustments. In these different adjustments the radio frequency voltage has different voltage characteristics and/or the generator has different electric characteristics. The different electric characteristics of the generator or its adjustments can be, for example, the internal resistance, the peak voltage, the modulation type of the radio frequency voltage, the modulation frequency of the radio frequency voltage, the maximum current of the radio frequency voltage or the like. The different adjustments of the generator or the different voltage characteristics lead to different ignition capabilities and/or different plasma maintenance capabilities.

The generator can be operated in one ignition operating mode at the start of a pulse and subsequently, during the pulse in an operating mode adapted to the desired effect. For example, at the beginning of a pulse the generator can be operated in a non-modulated operation (CW) and subsequently during the pulse in another operating mode, e.g. in a modulated (pulsed) mode. This operating mode can be configured according to the desired effect. For example, it can be desired to achieve a large area flat coagulation for Mucosa ablation.

It is, however, also possible to determine the operating mode at the start of the pulse during ignition and the subsequent operating mode after creation of the plasma for achieving an effect following different criteria. For example, in both phases the ignition ability and the plasma maintenance can be set according to different criteria, e.g. minimum secondary effect or other criteria.

The ignition ability thereby means any measure that indicates whether a plasma ignition can be carried out under the actual conditions and if so, to what extent the electrode distance (or electrode tissue distance) can be increased until no ignition takes place. The actual conditions mean all physical parameters that influence the ignition process, as for example the dimension of the electrode and the shape of the electrode, the electrode distance, the gas composition, the humidity of the tissue, the type of tissue, the temperature of the tissue, of the gas and of the electrode(s) etc.

The plasma maintenance ability means any measure that indicates whether a plasma may be maintained under the actual conditions and if so, to what extent the electrode distance (or electrode tissue distance) can be increased until the plasma extinguishes.

With regard to the plasma maintenance the actual conditions mean all of the physical parameters that influence the plasma maintenance, as for example the dimension of the electrode and the shape of the electrode, the electrode distance, the gas composition, the humidity of the tissue, the type of tissue, the temperature of the tissue, of the gas and of the electrode(s) etc.

An instrument that is to be supplied with a treating current or a probe with at least one electrode is connected or connectable to the generator. Via the electrode a plasma is fed that serves or is suitable for influencing on a biological tissue.

A plasma sensor is connected to the generator and/or the instrument by means of which the behavior of the plasma is detectable. A control device for influencing the adjustment of the generator is connected to the plasma sensor and the generator. The influence of the adjustment is thereby carried out based on the determined ignition capability and/or plasma maintenance capability determined by the control device. The control device is thereby configured in a way that it sets a suitable adjustment for the generator based on the behavior of the plasma detected by the plasma sensor. If the control device has determined a reliable ignition and/or reliable plasma maintenance, it thereby selects an adjustment with lower ignition capability and/or lower plasma maintenance as a trial. If in doing so and under the actual operation conditions of the connected instrument a spark can be reliably ignited and/or a plasma can be maintained, the control device does not change back to the previous adjustment of the generator. Preferably it can be additionally provided that the generator switches back to an adjustment with improved ignition capability or plasma maintenance capability, e.g. to the previous adjustment of the generator, if a plasma cannot be reliably ignited during the trial adjustment anymore and/or the plasma is not reliably maintained.

The generator is configured to create a radio frequency voltage with different voltage forms in its different adjustments. In doing so, the generator can be configured that it can switch between two or more voltage forms or that it can also vary the voltage form in a stepless manner. A voltage form can mean any feature of the radio frequency voltage that influences the ignition capability and/or the plasma maintenance capability thereof. Particularly, the voltage form can refer to at least one of the following parameters: the frequency, the peak voltage, the mean value, the root mean square value, the shape of the curve, the envelope with which the radio frequency voltage is modulated, the amplitude of the envelope, the shape and/or frequency thereof, the pulse/pause ratio (in case the radio frequency voltage is switched on/off) or similar parameters. The radio frequency voltage can be pulsed in a single or multiple manner, wherein the different voltage forms can distinguish by the length of the impulses and/or the length of the pauses between impulses. Among the different voltage forms there can be a voltage form, in which the generator is non-pulsed, i.e. it operates with a pause duration of zero. The pulsed wave forms comprise typically a pulse with one or more radio frequency oscillations that decay in a damped manner at the end of the pulse. These and other possibilities to influence the ignition capability and/or the plasma maintenance capability by the voltage form can also be combined.

Basically the different voltage forms provided by the generator in different adjustments can distinguish by different features, e.g. by the peak voltage, the mean value, the root mean square value, the constant component, the wave form, the envelope, the amplitude of the envelope, the shape thereof, the time-dependent progression, the frequency or other electric and/or time parameters, the pulse/pause ratio in case of an radio frequency voltage switched on/off and/or combinations thereof.

In a preferred embodiment the radio frequency voltage is pulsed and the different voltage forms distinguish primarily or exclusively by the duration of the pulses and/or the duration of the pauses between the pulses. In doing so, the pulse frequency can be constant or variable. Similarly the pulse/pause ratio (duty cycle) can be constant or variable and can, e.g. also comprise the pulse/pause ratio of 100:0 ("Continuous Wave").

The different adjustments of the generator typically lead to treatment currents with which similar or different desired physiological effects at the tissue can be achieved. Concurrently they also lead to different secondary effects, as for example light occurrences, noise occurrences, pressure impulses etc. Additionally, the plasma temperature can be selectively influenced up to the creation of a cold plasma that does not show any thermal tissue effect by means of the treatment currents and the different generator adjustments.

The instrument that is part of the device comprises at least one electrode that is connected or connectable with the generator via a conductor. Upon activation of the instrument the electric conductive plasma provided for treatment bridges, e.g. in the form of a spark, a distance between the electrodes or between the electrode and the biological tissue, wherein the biological tissue can also be connected with the generator. For example, the connection of the tissue with the generator can be carried out via a neutral electrode attached to the patient, a second electrode integrated into the instrument, an additional plasma path or via the capacitive coupling of the generator and the patient with the ground potential. The treatment current can also flow as displacement current under use of the capacity of the tissue.

The instrument can comprise a gas-guiding channel in or at which the electrode is arranged. The gas-guiding channel is connected to a gas source at its proximal end, e.g. an argon source, such that a gas jet can flow out of its distal end, in which an electric conductive plasma, e.g. in form of a spark, can be created by ionization.

Preferably the radio frequency voltage is pulsed with a medium frequency that is, for example, lower than one-fifth of the frequency of the radio frequency voltage, however, for example, preferably larger than one-twentieth thereof. The frequency of the radio frequency voltage is, for example, in a frequency range between 100 kHz and 20 MHz and has an amount of 350 kHz for example. The medium frequency is, e.g. in a range from 10 kHz to 100 kHz. It can have an amount of, e.g. 20 kHz, 30 kHz, 45 kHz or 50 kHz. The voltage forms that are available for the generator and that are selectable by the control device may distinguish by the pulse length, if the frequency is e.g. set to 45 kHz or 50 kHz, wherein the assortment of available voltage forms can also contain pulse sequences with lower or higher frequency.

Additionally the radio frequency voltage that is pulsed with the medium frequency can be pulsed with a low frequency that has an amount of preferably at least 0.5 Hz and however further preferably at most 200 to maximum 500 Hz. A preferred frequency range of the low frequency ranges from 1 Hz to 100 Hz. The voltage forms of the radio frequency can distinguish as required by different pulse lengths and/or different pause lengths of the low frequency. The pause length can also be zero.

The plasma sensor serves to determine the behavior of the plasma at the treatment instrument. As the generator and the control device, the plasma sensor can also form part of a device for supply of the instrument. The plasma sensor detects at least one parameter characterizing the presence or absence and/or the quality or stability of the plasma. For example, this can be carried out in an indirect manner by configuration of the plasma sensor to detect the voltage transmitted to the instrument and/or the current flowing to the instrument and to monitor these parameters or parameters derived therefrom. For example, the plasma sensor can determine the effective impedance at the instrument from the detected voltage and the detected current, wherein the effective impedance is composed substantially of the impedance of the plasma and the impedance of the biological tissue. This impedance and/or its time-dependent change can be used as indicator for the plasma stability and/or plasma quality. In additional embodiments also other parameters and/or their time-dependent change can be used as measure for the quality or stability of the plasma, wherein the parameters can be measured by appropriate sensors and/or can be derived from measurement values. Such parameters are, e.g. the electric current, the electric power, further measured or calculated characteristics of the electric current, of the electric voltage and/or a combination thereof, the intensity and/or the spectrum of an optical light occurrence, the temperature of the gas or plasma, the electric and/or magnetic field and/or the electromagnetic radiation of the plasma. These or other suitable parameters can be used individually or in combination as described above in order to determine the plasma stability and/or plasma quality.

The control device connected to the plasma sensor is configured to select the generator adjustment based on the behavior of the plasma detected by the plasma sensor and to cause the generator to output a voltage with specific voltage characteristics. In doing so, the control device can be further configured to determine the generator adjustments when the treatment instrument is activated based on occasional or perpetual tests. In doing so, the control device can be configured to first check the ignition behavior and/or the plasma maintenance behavior with the actual generator adjustment and if the ignition or plasma maintenance behavior is insufficient, to select a generator adjustment with improved ignition capability and/or plasma maintenance capability. Additionally, the control device can be configured to select a generator adjustment with a lower ignition capability and/or plasma maintenance capability and to cause the generator to transition to such an adjustment, if the control device has determined a reliable quick ignition and/or a reliable maintenance of the plasma at least one time and preferably a plurality of times. It can be provided that the generator adjustment is at first maintained, if it allows a reliable operation. If not, it is changed to the previous or another generator adjustment with improved ignition capability and/or improved plasma maintenance.

With this device on one hand a reliable ignition and maintenance of the plasma during coagulation is allowed without the need to operate with an at least temporary excess of power, peak voltage, frequency or one or more other parameter characterizing a voltage form of the respective generator adjustment for this purpose. Such an excess means a generator adjustment, in which the ignition capability and/or the plasma maintenance capability of the radio frequency voltage is larger than necessary. By ignition of the plasma without (or with at least low and in the best case lowest possible) excessive undesired secondary effects of the plasma ignition and/or of the current flowing through the plasma can be suppressed largely, such that the tissue and/or the instrument are not (or not more as necessary) damaged and the treating person is neither blinded nor startled. Such undesired secondary effects can be, e.g. the creation of very bright light occurrences or the creation of bang noises, undesired tissue damages, instrument damages or the like. Due to the stepwise approximation of the adjustment of the generator at the lowest possible adjustment (i.e. the adjustment that just allows an ignition and/or a stable plasma maintenance), undesired secondary effects can be minimized. On the contrary, desired effects of the plasma ignition and/or of the current flowing through the plasma can be maximized or selectively influenced otherwise, e.g. by a respective selection of the available adjustments.

At the start of the activation of the instrument as well as the start of each pulse of the low frequency if applicable, a plasma has to be ignited respectively. In each low frequency pulse a medium frequency sequence of high frequency pulses can be comprised. The control device is preferably configured that it operates the generator with the adjustment that leads to the creation of a plasma within an ignition trial duration at minimum ignition capability of the voltage form during the operation of the instrument, i.e. during the application thereof with different high frequency voltage forms. In doing so, the adjustment is used that has at least one characteristic that influences the ignition of the plasma, e.g. the pulse/pause ratio, just in the necessary amount, but however not in excess. In doing so, undesired effects involved with the ignition of the plasma are minimized, i.e. the effects of the ignition are influenced in a desired manner.

The control device is preferably configured, such that it further operates the generator with an adjustment with improved ignition capability, e.g. by an increased pulse/pause ratio, during the operation of the instrument and after expiration of the ignition trial duration, if within the ignition trial duration no creation of the plasma has been detected by the plasma sensor. In doing so, it is achieved that the ignition of the plasma is effected with a voltage form that is just enough ignition capable in order to effect a reliable ignition, however, not unnecessarily more ignitable.

A similar strategy as for the ignition of the plasma can be applied for its maintenance during the treatment phase. In doing so, the control device is configured such that it operates the generator after expiration of an ignition phase in a treatment phase with an adjustment that allows the maintenance of the plasma with a minimum plasma maintenance capability of the voltage form. In other words, it selects the adjustment for the operation during the treatment phase that on one hand guarantees the plasma maintenance and on the other hand is the adjustment among the adjustments of the generator, at which a selected secondary effect is as low as possible. The secondary effect is, e.g. the light occurrence, the noise creation, the tendency to puncture the tissue, the plasma temperature, particularly its ion temperature or the like. The same control strategy is used for the ignition phase.

For this the control device can be configured, such that it operates the generator with an actual adjustment during the operation of the instrument after the plasma has been build up and in so doing monitors the plasma stability. If an impeding extinction or even an extinction of the plasma is determined, the control device changes to an adjustment with improved plasma maintenance, e.g. by an increased pulse/pause ratio of the radio frequency voltage. Alternatively or additionally the control device can set an adjustment after the subsequent ignition phase that provides an improved plasma stability, e.g. due to an increased pulse/pause ratio of the radio frequency voltage, if the plasma was stalled or became instable. If however during the treatment with an actual voltage form no impeding extinction, but a stable plasma maintenance was determined during a specific duration, the control device can select as a trial an adjustment with decreased plasma maintenance capability, e.g. due to a lower pulse/pause ratio, in order to minimize and/or influence light and noise occurrences, power application, tissue effects and other effects of the plasma jet during the treatment phase in a desired direction.

By setting the adjustment of the generator at which the medium frequency comprises a minimum pulse/pause ratio, the radio frequency voltage comprises a minimum peak voltage or another characteristic influencing the power application, the power application is influenced, particularly minimized, during the treatment phase of a pulse of the low frequency. However, in order to be able to realize a desired average power application, the control device can be further configured that the pulse/pause ratio of the low frequency or another feature of the voltage form that influences the power application is adjusted that the average power effectively supplied to the instrument is equal to a desired value. If the control device selects a voltage form with higher power application during the pulse of the low frequency, it can thus reduce, i.e. balance, the power application again that was increased thereby, by for example reducing or inverting the pulse/pause ratio of the low frequency. In doing so, it is possible to provide different operating modes that comprise different ignition capabilities and/or plasma maintenance capabilities, but thereby having the same power application.

The inventive method can be configured, e.g. such that the radio frequency power during one pulse of a pulsed radio frequency alternating voltage pulsed with low frequency is limited or minimized. Each low frequency pulse contains a medium frequency sequence of high frequency oscillations. The power of the low frequency pulses is e.g. adjusted as low as possible. By adapting the low frequency pulse/pause ratio, the desired power can still be provided in the average. The treatment is carried out with low light and noise generation.

BRIEF DESCRIPTION OF THE DRAWINGS

Further details of advantageous embodiments of the invention are subject of dependent claims, the drawings and the respective description. The drawings show:

DETAILED DESCRIPTION

Figure 1:
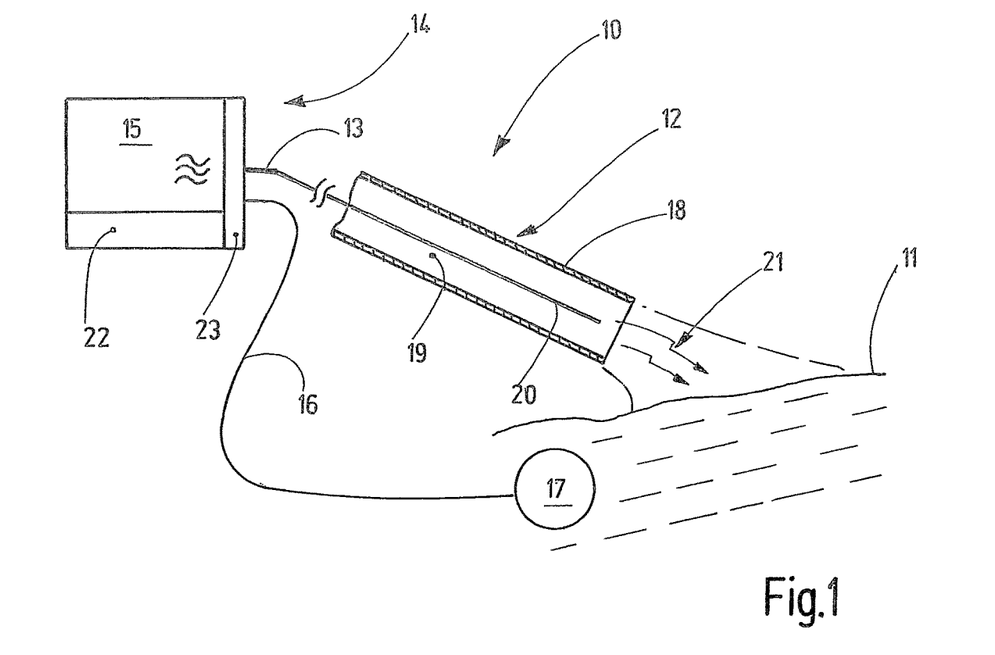
FIG. 1 a treatment device in a highly schematic illustration.

FIG. 1 illustrates device 10 for plasma treatment of biological tissue 11, e.g. during a surgical procedure. An instrument 12 belongs to the device 10, e.g. in form of an instrument used for open surgery or in form of a rigid or flexible probe that can be used in an endoscope. For supply of the instrument 12 it is connected with an apparatus 14 via a conductor 13, wherein the apparatus 14 comprises a generator 15 for supply of the instrument 12 with radio frequency current.

The generator 15 is configured, such that it outputs a radio frequency voltage to the instrument 12 upon activation of the instrument 12, wherein the generator 15 is able to operate in different adjustments. Each of the adjustments of the generator distinguishes in at least one electric characteristic from all other adjustments. An electric characteristic can be the form, frequency, modulation type, crest factor, pulse/pause ratio of a generated pulsed radio frequency voltage, the amount of the radio frequency voltage, the internal resistance of the generator, the maximum current or the like. This is illustrated in FIGS. 3A to 3D exemplarily with different pulse/pause ratios of a pulsed radio frequency voltage.

The apparatus 14 can be further connected with a neutral electrode 17 via a neutral conductor 16, wherein the neutral electrode 17 is attached at biological tissue 11, e.g. at the skin of a patient, in a large area. Alternatively the instrument 12 can be configured as bipolar instrument and in so doing, comprise at least two electrodes.

The instrument 12 comprises a channel 19 formed by a rigid tube or a flexible hose 18 as well as an electrode 20 that terminates shortly ahead, at or behind the distal end of the hose 18 in order to create a plasma 21 extending to the tissue 11. The channel 19 is connected to a non-illustrated gas source and is thus flowed through with a gas, e.g. argon, that exits at the distal end of the hose 18 and in which the plasma 21 is created between the electrode 20 and the tissue 11. The invention can also be used with instruments without gas supply.

The apparatus 14 comprises a control device 22 additionally to the generator 15, wherein the control device 22 is configured to set the operating mode of the generator 15 and by means of which the generator 15 can be switched on and off. The control device 22 is, e.g. configured to predefine the voltage form that has to be supplied by the generator 15.

Additionally, the apparatus 14 comprises a plasma sensor 23 that detects the voltage between the conductor 14 and the neutral conductor 16 as well as the current flowing in the conductor 13 and/or the conductor 16 and derives therefrom a parameter characterizing the presence or absence of the plasma as well as the quality thereof. In the simplest case this parameter is the detected current itself. It is, however, also possible to configure a plasma sensor, such that it derives derived parameters for characterizing the plasma quality from the detected voltage and/or the detected current. Such parameters can be, e.g. the amount of the flowing current, the velocity or rate of the change of the current, the impedance calculated as quotient between the detected voltage and the detected current, the change of the impedance (increase of the impedance and/or decrease of the impedance), the velocity or rate of the change of the impedance, impedance fluctuations, current distortion factors, the content of harmonics in the current, the crest factor of the current, the difference between the harmonics content of the current and the harmonics content of the radio frequency voltage or similar parameters.

For plasma treatment the treatment instrument 12 is preferably supplied with a radio frequency voltage HF created by the generator 15 that preferably has a frequency between 100 kHz and 20 MHz and in the present embodiment 350 kHz. The radio frequency voltage HF is typically pulsed with a medium frequency MF and additionally with a low frequency NF. The created low frequency pulse packets P1, P2, P3 that succeed each other can have a duration from 2 msec up to two seconds. Between the pulse packets P1, P2, P3 are pauses of nearly two seconds down to almost zero seconds, depending on the pulse/pause ratio. Within the pulse packets P1, P2, P3 the generator 15 provides a radio frequency voltage HF with different voltage forms. Characteristics thereof can be adjusted at the generator 15 and/or the control device 22 by means of a provided user interface and/or communication interface for connection with additional devices, e.g. mobile and devices, as necessary. In doing so, treatment influencing parameters, as for example the peak value of the radio frequency voltage, the maximum current, the desired power, the treatment duration or similar can be adjustable. Additionally, means for selection or limitation of selectable adjustments of a generator can be provided as required among which the control device 22 can select a suitable adjustment and the voltage form derived therefrom for the operation of the generator 15.

Figure 2:
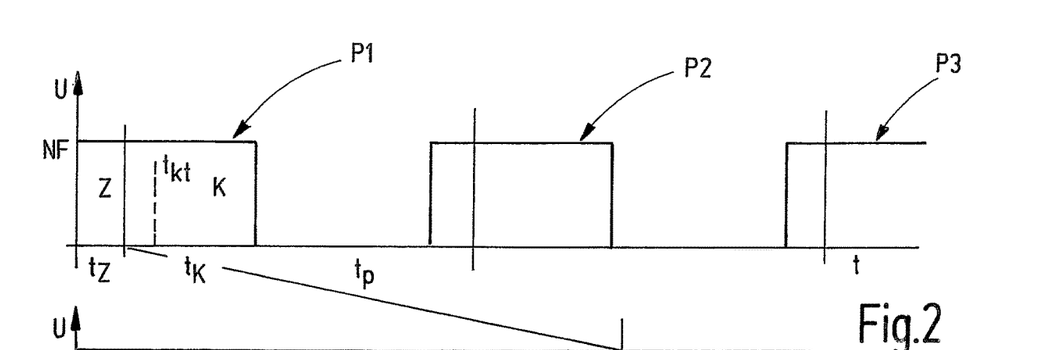
FIG. 2 a low frequency envelope with a radio frequency voltage pulsed at medium frequency for clarification of the operation of the device according to FIG. 1, FIG. 3 a pulse of the pulse sequence according to FIG. 2 in a stretched illustration, FIG. 3A to 3D different voltage forms of the radio frequency generator oscillation pulsed at a medium frequency with different pulse/pause ratios within one pulse according to FIG. 3 as voltage forms for ignition operation and/or treatment operation, FIG. 4 a flow diagram as an example for appropriate selection of a voltage form for the ignition operation for clarification of the function of the control device, FIG. 5 a flow diagram as an example for clarification of the operation of the control device in the treatment operation.
Figure 3:
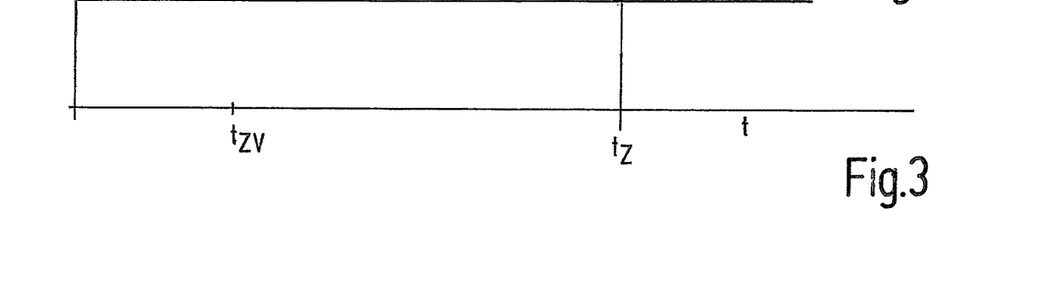

The pulse packet P1 of the low frequent succeeding pulse packets P1, P2, P3 as exemplarily shown in FIG. 2, is shown in FIG. 3 in an enlarged manner. It is divided in an ignition phase Z and a treatment phase K. The ignition phase Z serves to build up plasma and for a stable ionization thereof. The duration $t_Z$ provided for this purpose can comprise an ignition trial duration $t_{ZV}$, as illustrated in FIG. 3 that can be defined duration of, for example 1 msec or a defined fraction of the ignition phase duration $t_Z$. Within this ignition trial duration $t_{ZV}$ it is monitored whether the ignition of the plasma or the spark has occurred when the radio frequency voltage is applied.

Figure 3A:
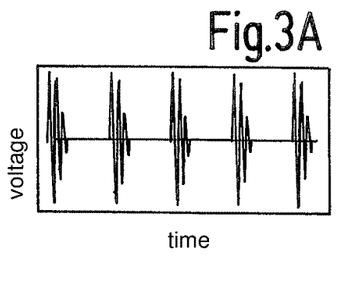

During the ignition, i.e. at least until the expiration of the ignition trial duration $t_{ZV}$ the generator 15 operates controlled by the control device 22 with an initial adjustment that is selected among a plurality of possible predefined adjustments. FIGS. 3A to 3D show voltage forms of the respective adjustments that preferably comprise coincident radio frequency and peak voltage. They are pulsed with a medium frequency modulation voltage. For example, pulse frequency has any frequency amount between 10 kHz and 70 kHz. After one or more undamped oscillations the high frequency voltage settles, i.e. it decays in a damped manner. FIG. 3A illustrates an adjustment with a high pulse/pause ratio. The medium frequency modulation frequency has an amount of 50 kHz in this case. This voltage form comprises the best ignition characteristics among the available voltage forms, but however also the most powerful light and noise development.

Figure 3B:
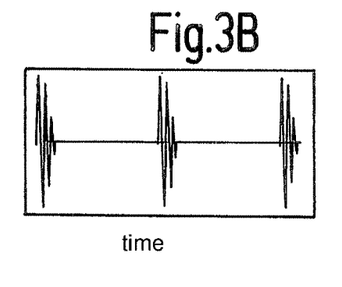

FIG. 3B illustrates a second adjustment, in which the medium frequency modulation frequency is set to 40 kHz. This voltage form comprises good ignition characteristics with extenuated light and extenuated noise development.

Figure 3C:
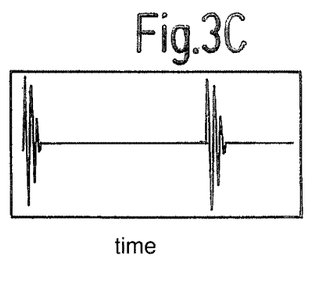

FIG. 3C illustrates a third adjustment, in which the radio frequency voltage HF is modulated with a medium frequency MF of 30 kHz, such that the pulse/pause ratio is further decreased compared with FIG. 3B. At slightly degraded ignition characteristics the light and noise development is further reduced.

Figure 3D:
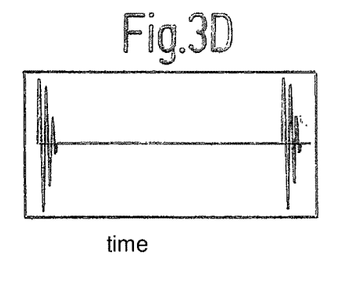

FIG. 3D illustrates another adjustment that can be selected by the control device 22 and provided by the generator 15, if applicable. The duty cycle and the frequency of the medium frequency MF are again reduced. It is still within the indicated range of 10 to 70 kHz and has an amount of, for example 20 kHz in this case.

During the ignition phase Z the device 10 operates as follows:

The control device 22 selects one of the indicated four adjustments explained above according to FIG. 3A to 3D for ignition of a plasma at the start of the pulse packet P1. This procedure is illustrated in block 30 of FIG. 4. At the start of the treatment the control device 22 selects the adjustment, e.g. according to a manual specification or according to a last used adjustment. The time counters $t_{ign}$ and $t_{Vform}$ are initially set to zero. Then the generator 15 starts the creation of the radio frequency voltage (see block 31). Within the time duration $t_{meas}$ the measurement values, e.g. current, voltage and other parameters, are detected and derived parameters, e.g. the value of the plasma sensor 23 are calculated. The time counters are respectively increased by $t_{meas}$. Subsequently it is checked whether a plasma has been created or not (block 32). If this is not the case, it is checked whether the ignition trial duration $t_{ZV}$ has expired (block 33). If this is the case, the ignition trial is terminated and an ignition pause is inserted (block 36). If not, it is checked whether the ignition trial duration provided for one voltage form $t_{ZV\_Vform}$, that is shorter than $t_{ZV}$ (e.g. one quarter of the available ignition duration $t_{ZV}$ or a defined duration of at least 1 msec) has been expired (block 34). If one of the two ignition trial durations has expired without the plasma having ignited, the control device selects the voltage form with higher ignition capability, as illustrated in block 35. Concurrently the time counter $t_{Vform}$ for a voltage form is reset. If the control device 22 has defined, for example, the voltage form according to FIG. 3C, initially it now changes to the voltage form according to FIG. 3B. According to block 31, again a measuring duration is passed and then it is checked whether a plasma has ignited. If this is not the case until the expiration of one of the ignition trial durations, again a voltage form with even higher ignition capability is selected in block 35, e.g. the voltage form according to FIG. 3A.

Figure 4:
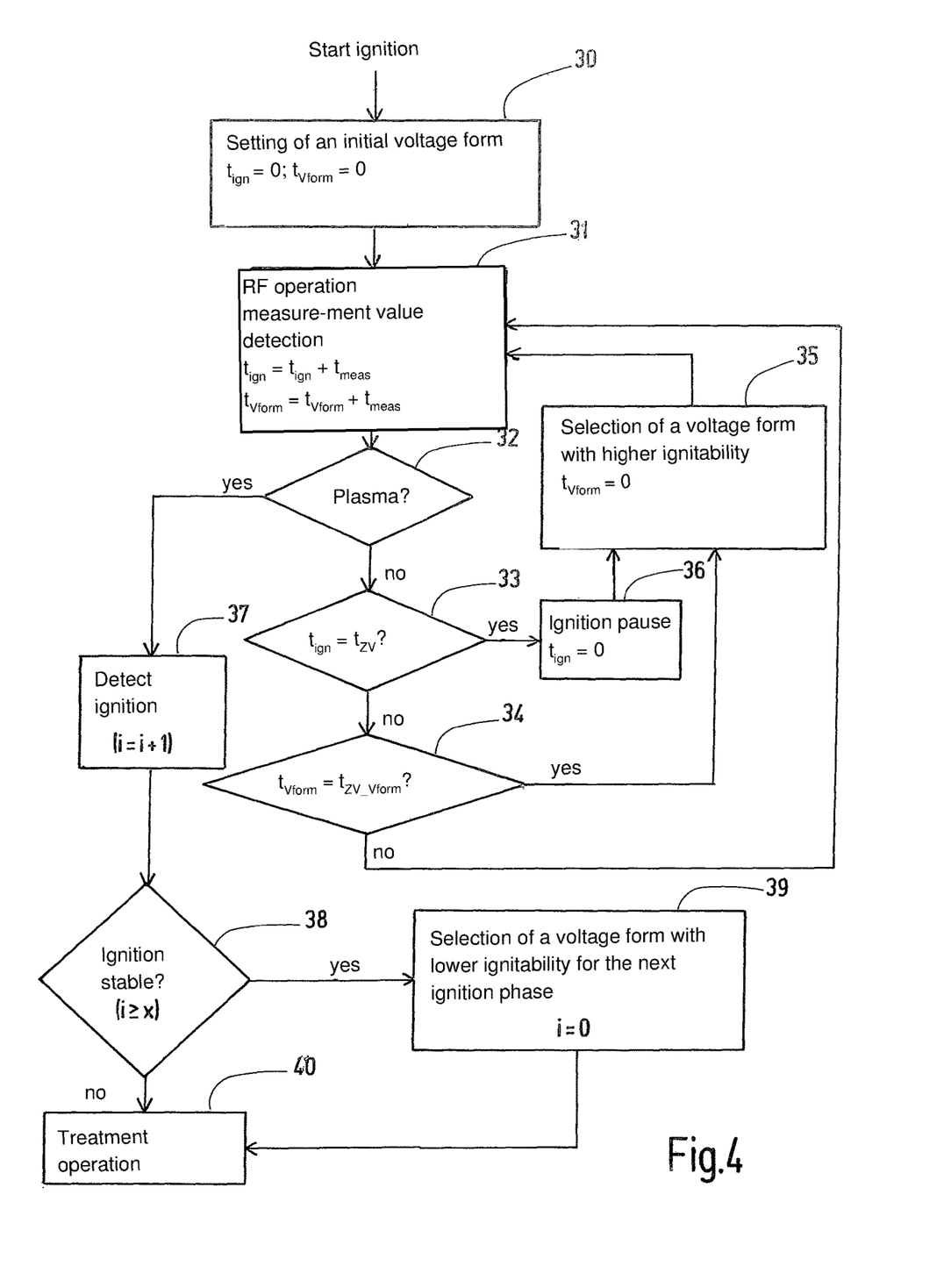

If a plasma has ignited, the successful ignition is registered, e.g. by incrementing a counter variable i in block 37. In block 38 it is checked whether the number X of successful ignition trials has been reached. If this and/or another stability criteria is fulfilled, the control device 22 changes to a voltage form with less ignition capability for the next ignition phase of the low frequency with concurrent reset of the counter variable i, in order to test whether the ignition can also be effected with lower light and noise development. Subsequently, it is directly transitioned into the treatment operation (block 40).

The treatment operation K follows the ignition operation, wherein in turn different adjustments according to FIGS. 3A to 3D are provided for the treatment operation K. The voltage form according to FIG. 3A has the best plasma maintenance characteristics, the largest average power and the most intense light and noise deviation. The voltage forms according to FIGS. 3B, 3C and 3D have from left to right a respective decreased plasma maintenance capability, a lower average power and a lower light and noise development as the preceding voltage form in the sequence.

For the treatment phase the same, as in this example, but also another selection of voltage forms can be used compared with the ignition phase.

Figure 5:
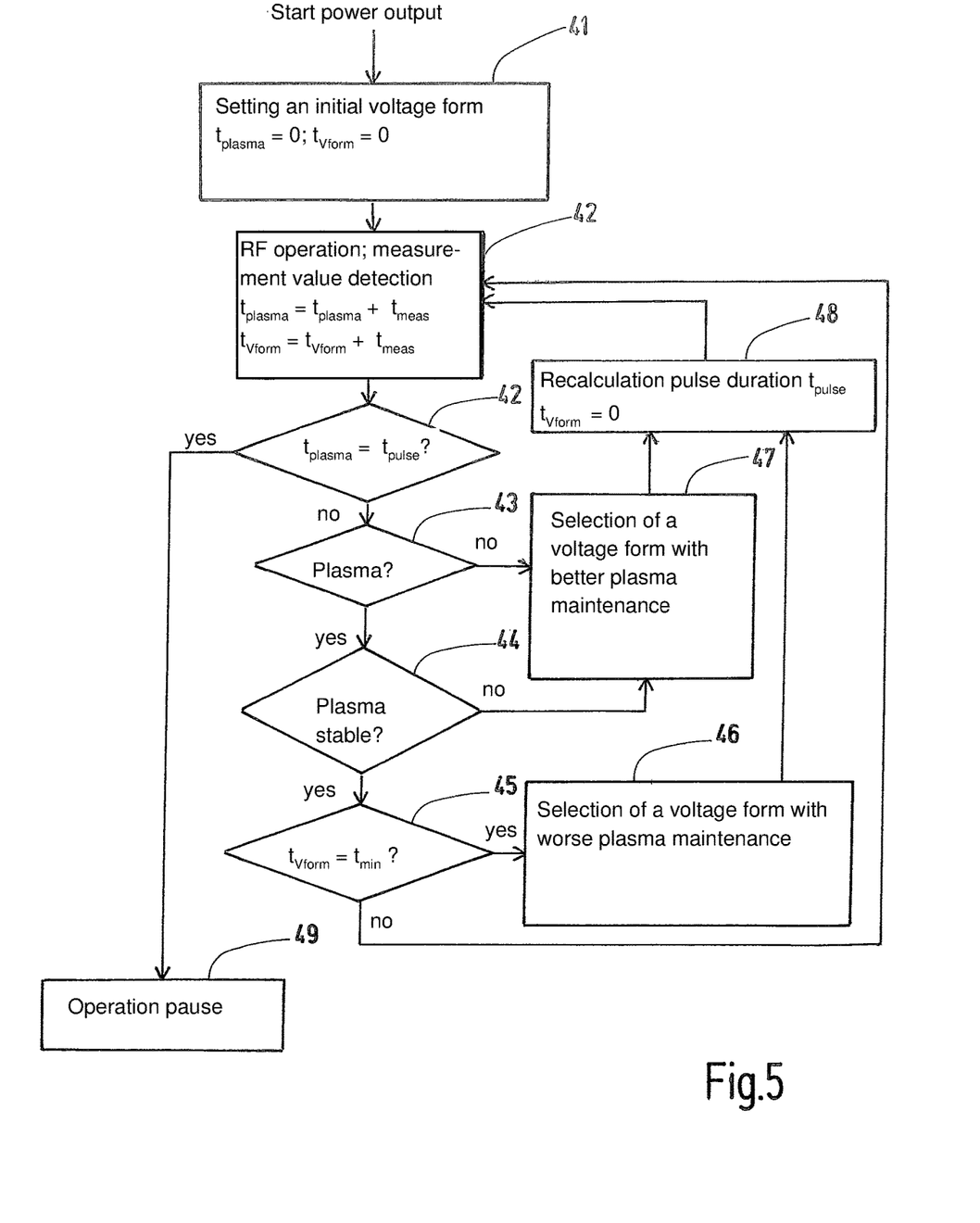

In the treatment phase K the device 10 operates as follows:

At the start of the treatment phase it is operated with an initial voltage form as symbolized in block 41. This voltage form can be predefined, for example, or can be derived from the history and can correspond to the last successfully used voltage form. The time counters $t_{plasma}$ and $t_{Vform}$ needed in the further procedure are initially set to zero. The voltage form is supplied to the instrument 12, as symbolized by block 42. Within a duration $t_{meas}$ measuring values are detected and derived parameters, e.g. the value of the plasma sensor 23 is calculated, as in the ignition phase. The time counters are respectively increased by $t_{meas}$. Subsequently the time counter $t_{plasma}$ is compared with a duration $t_{pulse}$ defined by the adjusted power application (block 42). If the duration $t_{pulse}$ has lapsed, a change to an operating pause is carried out (block 49). Otherwise the condition of the plasma is retrieved by means of the plasma sensor. In a preferred embodiment the plasma sensor is configured to detect not only an interruption of the plasma (block 43), but also a prefigured interruption of the plasma (block 44). For this it can be, for example, configured to monitor the impedance that can be measured between the conductors 13 and 16 and its time-dependent progression. If the impedance increases within a given duration of, for example 200 μs about more than for example 10% or a defined value, for example 200 Ohm, this is an indicator for an impending plasma interruption. The plasma sensor 23 can be configured to detect this. The control device 22 can be additionally configured to immediately select an adjustment with improved plasma maintenance characteristics when an indicator for an impending plasma interruption according to block 44 is present (block 47). For example, it transitions from a voltage form according to FIG. 3D to a voltage form according to FIG. 3C from a voltage form according to FIG. 3C to a voltage form according to FIG. 3B or from a voltage form according to FIG. 3B to a voltage form according to FIG. 3A. Finally the control device 22 jumps in block 44 in the sequence of voltage forms of FIG. 3A to FIG. 3D respectively about at least one step to the left.

If the plasma is stable during a duration of at least $t_{min}$, the control device selects as a trial a voltage form with decreased plasma maintenance characteristics, by jumping in the sequence of voltage forms of FIG. 3A to 3D about at least one step to the right. The duration $t_{min}$ can thereby be individually defined for each voltage form. If, for example, the treatment during the duration $t_{min}$ has been successfully been carried out with the voltage form according to FIG. 3B, the control device changes to the voltage form according to FIG. 3C. If a plasma instability shows, it is changed back to the voltage form according to FIG. 3B. If, however, the plasma remains stable with the voltage form of FIG. 3C, the light and noise occurrence is minimized.

With the presented manner the control device 22 respectively selects the wave form for ignition and treatment that involves the lowest possible undesired secondary effects, as light and noise development. The control device can influence one or more other effects of ignition and/or the plasma stream in the desired direction, whereas on the other hand a reliable ignition and reliable plasma treatment is achieved. Due to the change of the adjustments of the generator 15 during the ignition and/or during the treatment within and between the individual pulse packets P1, P2, P3, the power transferred to the biological tissue 11 can be influenced. The control device 22 has the minimizing object to select a voltage form in the FIGS. 3A to 3D as far to the right as possible respectively, i.e. a voltage form with a duty cycle that is as low as possible. This goes along with a reduced power application.

However, to guarantee the desired average power application $P_{des}$, the control device 22 can be configured to increase or decrease the duration of the pulse packets P1, P2, P3, as it is illustrated by block 48 in FIG. 5. For this the control device 22 can be configured to detect the energy transmitted so far to the biological tissue in a pulse packet and to calculate the duration $t_{pulse}$, such that the transferred energy after expiration of the duration $t_{pulse}$ is equal to the product of the desired power $P_{des}$ and the total duration $t_T$. The total duration $t_T$ is the sum of the ignition phase duration $t_Z$, the treatment phase duration $t_K$ and the pause duration $t_P$ and has an amount of, 20 msec with a defined low frequency of 50 Hz, for example.

Modifications of the treatment phase are possible. For example the control device can check after expiration of a specific duration, e.g. 0.5 msec or a portion of the predefined duration of the pulse packet whether the plasma is still present and if this is the case, to change to a voltage form with decreased plasma maintenance characteristics, but in exchange with lower noise and light development. If in so doing, the plasma is interrupted or then shows lack of stability, a change back to a voltage form with better maintenance characteristics can be initiated by the control device within the same treatment phase.

Independent therefrom in all presented embodiments the duration of the pulse packets P1, P2 and/or P3 can be adapted at each change of the voltage form according to the characteristics of the formerly and actually used voltage form in order to maintain the average power P introduced in the tissue as constant as possible.

The selection of the adjustments for the ignition and treatment phase can be selected in each pulse packet, as it was last used in the previous ignition and treatment phase. For example, the pulse packet P2 can start with the adjustment with which the ignition was at last effected in the pulse packet P1. The same applies for the voltage form for treatment.

Whereas according to the description above, a change between the different voltage forms according to FIGS. 3A to 3D has been emanated in the sense of switching, this change can be carried out in a floating manner or stepless, if required.

In a modified embodiment of the apparatus 14 the control device 22 is configured to check the impedance measured by the plasma sensor 23 whether it is within a predefined value range, e.g. between 100 Ohm and 9.5 kOhm. If this is the case, a control device 22 can assume the presence of a plasma. Alternatively, the amount of the measured root mean square current can be provided as indicator. In this case, the plasma sensor 23 is configured to detect whether the measured root mean square current is larger than a predefined value of, e.g. 0.1 Ampere. Additionally, the plasma sensor 23 can be configured to monitor the impedance. If it is smaller than a predefined value of, for example 3 kOhm, this can serve in combination with the above-mentioned threshold exceedance of the current as an indicator for the presence of a plasma. Also other parameters and their combinations and other thresholds can be used.

The presented device 10 adapts at least during one of the phases for ignition and treatment the used voltage form dynamically in order to obtain a best possible compromise between ignition and maintenance of the plasma and minimization or maximization of desired or undesired effects of the ignition and/or the plasma current. The plasma sensor monitors parameters and/or their change characterizing the condition of the plasma during the treatment phase in order to determine a prefigured interruption of the plasma and, in the ideal case, avoid this by already changing the voltage form previously.

The indicated mechanisms can be used by the control device 22 also during a pulse packet P1, P2, P3. The length of each pulse packet is adapted at each change of the adjustment according to their characteristics in order to guarantee a constant average power.

The method for plasma treatment is directed to cause the radio frequency generator 15 for ignition of a plasma at the instrument 12 and for maintenance thereof by a respective output of a medium frequency pulse with modulated radio frequency voltage, a duty cycle thereof is just as high that it is sufficient to ignite and maintain the spark, but not higher. In doing so, noise and light occurrences are minimized. The definition of the duty cycle on the minimum possible value can be carried out step by step by continuous or occasional variation of the adjustment under monitoring the ignition capability and the plasma maintenance. The adjustment of the duty cycle optimized by the method can be carried out continuously without steps or with steps by selection of different voltage forms from a stock of voltage forms. By minimization of the duty cycle of the medium frequency, the desired low light and low noise of the treatment process is obtained. By inverse modulation of the duty cycle of the low frequency, the desired power is adjusted.

REFERENCE SIGNS

10 device
11 biological tissue 12 instrument
13 power
14 apparatus
15 generator
16 neutral conductor
17 neutral electrode
18 hose
19 channel
20 electrode
21 plasma
22 control device
P1, P2, P3 pulse packets
30-46 blocks

The invention claimed is:

1. A device (10) for plasma treatment comprising:
a generator (15) that is configured to create a radio frequency alternating voltage (HF) in different adjustments, an instrument (12) that is connected or connectable to the generator (15) for supplying the instrument with a treatment current, wherein the instrument (12) comprises at least one electrode (20) to which the radio frequency alternating voltage (HF) is fed for creating a plasma at the electrode (20), wherein the radio frequency alternating voltage created in the different adjustments comprise at least one of different ignition capabilities and different plasma maintenance capabilities,
a control device (22) that is connected to the generator (15) for adjustment of the generator (15), such that the generator (15) is started in an ignition operating mode and then operated in an operating mode,
a plasma sensor (23) that is connected to at least one of the generator (15) and the instrument (12) to determine a behavior of the plasma at the instrument (12),
wherein the control device (22) is connected to the plasma sensor (23) to allow adjustment of the generator (15) by the control device (22) based on the behavior of the plasma detected by the plasma sensor (23),
wherein the control device (22) is configured to at least one of:
determine an adjustment of the different adjustments with at least one of reduced ignition capability and reduced plasma maintenance capability for the generator (15), based on the behavior of the plasma detected by the plasma sensor (23), if the behavior of the plasma characterizes at least one of a reliable ignition behavior and a reliable plasma maintenance, and
determine an adjustment of the different adjustments with at least one of increased ignition capability and increased plasma maintenance capability for the generator (15), based on the behavior of the plasma detected by the plasma sensor (23), if the behavior of the plasma characterizes at least one of a non-reliable ignition behavior and a non-reliable plasma maintenance, and
wherein the control device (22) is configured to operate the generator (15) during operation of the instrument (12) in a treatment phase with a voltage form that is pulsed at a medium frequency (MF) having a pulse/pause ratio after build-up of the plasma has been achieved in an ignition phase, wherein the pulse/pause ratio is reduced for the treatment phase following a subsequent ignition phase, if a stable presence of the plasma has been detected by the plasma sensor within a treatment duration in at least one treatment phase and wherein the pulse/pause ratio is increased, if an extinction tendency of the plasma has been determined.

2. The device according to claim 1, wherein the different adjustments of the generator cause the generator to at least one of:
output voltages with different voltage characteristics, and
provide voltages at different generator characteristics,
wherein the different voltage characteristics comprise at least one of:
an amount of the voltage, a modulation type, a degree of modulation, a voltage form, a pulse/pause ratio, and a frequency, and
the generator characteristics comprise an internal resistance of the generator.

3. The device according to claim 1, wherein the radio frequency alternating voltage (HF) is pulsed with a medium frequency (MF) that is smaller than one-fifth of a frequency of the radio frequency alternating voltage (HF) and larger than one-twentieth of the frequency of the radio frequency alternating voltage (HF) and the control device (22) is configured such that voltage characteristics are distinguishable from each other by different pulse/pause ratios of the medium frequency (MF).

4. The device according to claim 1, wherein the radio frequency alternating voltage is pulsed with a low frequency (NF) that is at least 0.5 Hz and at most 200 Hz.

5. The device according to claim 1, wherein the control device (22) is configured to operate the generator during the operation of the instrument (12) with one of the different adjustments with a lowest secondary effect and which leads to a creation of plasma within an ignition trial duration.

6. The device according to claim 5, wherein the control device (22) is configured to operate the generator (15) in an adjustment of the different adjustments with increased secondary effect after the ignition trial duration has lapsed, if within the ignition trial duration no creation of plasma has been detected by the plasma sensor (23).

7. The device according to claim 5, wherein the control device (22) is configured to operate the generator at a subsequent ignition trial in an adjustment of the different adjustments with decreased secondary effect during the operation of the instrument (12) after at least a singular successful build-up of the plasma within the ignition trial duration.

8. The device according to claim 1, wherein the control device (22) is configured to operate the generator during operation of the instrument after lapse of an ignition phase in a treatment phase with an adjustment of the different adjustments that allows maintenance of the plasma at a minimum other secondary effect.

9. The device according to claim 8, wherein the control device (22) is configured to operate the generator (15) during operation of the instrument (12) in at least one of:
the treatment phase, and
a subsequent treatment phase,
with an adjustment of the different adjustments with at least one of:
a higher plasma maintenance capability, and
a higher secondary effect,
after build-up of plasma was achieved in the ignition phase, if within the treatment phase an extinction or an instability of the plasma was detected by the plasma sensor (23).

10. The device according to claim 9, wherein the control device (22) is configured to change the adjustment of the generator to an adjustment of the different adjustments with at least one of:

a lower plasma maintenance capability, and
a lower secondary effect,
if during the operation of the instrument (12) after the build-up of the plasma was achieved in the ignition phase no extinction tendency of the plasma was detected by the plasma sensor (23) during the treatment phase.

11. The device according to claim 1, wherein the plasma sensor (23) is configured for monitoring an electric parameter for detection of a stability of the plasma, wherein the monitoring of the electric parameter includes monitoring the time-dependent progression of the electric parameter, wherein the electric parameter is derived from at least one of the treatment current supplied to the instrument (12) and the radio frequency alternating voltage (HF) supplied to the instrument (12).

12. The device according to claim 1, wherein the different adjustments of the generator (15) comprise at least two adjustments that comprise at least one of:
different ignition capabilities,
different plasma maintenance capabilities,
adjustments that cause different light emissions, and
adjustments that cause different acoustic noise emissions,
wherein the at least two adjustments also output a constant average power in at least one of the plasma and a tissue.

13. A method for control of a device (10) for plasma treatment that comprises a radio frequency generator (15) for supply of an instrument (12), the method comprising:
operating the radio frequency generator (15) at one of a plurality of different adjustments, wherein in the plurality of different adjustments an alternating voltage (HF) output from the radio frequency generator comprises at least one of:
different ignition characteristics,
different plasma maintenance characteristics, and
alternating voltage (HF) outputs for which the created plasma comprises visible light and acoustic noise emissions of different intensity,
operating the radio frequency generator (15) for ignition and maintenance of a plasma at the instrument (12) in one of the plurality of different adjustments with at least one of a lowest visible light emission and lowest acoustic noise emission, that also allows ignition and plasma maintenance, and
operating the radio frequency generator (15) during operation of the instrument (12) in a treatment phase with a voltage form that is pulsed at a medium frequency (MF) having a pulse/pause ratio after build-up of the plasma has been achieved in an ignition phase, wherein the pulse/pause ratio is reduced for the treatment phase following a subsequent ignition phase, if a stable presence of the plasma has been detected within a treatment duration in at least one treatment phase and wherein the pulse/pause ratio is increased, if an extinction tendency of the plasma has been determined.

14. A device (10) for plasma treatment comprising:
a generator (15) that is configured to create a radio frequency alternating voltage (HF) in different adjustments,
an instrument (12) that is connected or connectable to the generator (15) for supplying the instrument with a treatment current, wherein the instrument (12) comprises at least one electrode (20) to which the radio frequency alternating voltage (HF) is fed for creating a plasma at the electrode (20), wherein the radio frequency alternating voltage created in the different adjustments comprise at least one of different ignition capabilities and different plasma maintenance capabilities,
a control device (22) that is connected to the generator (15) for adjustment of the generator (15), such that the generator (15) is started in an ignition operating mode and then operated in an operating mode,
a plasma sensor (23) that is connected to at least one of the generator (15) and the instrument (12) to determine a behavior of the plasma at the instrument (12),
wherein the control device (22) is connected to the plasma sensor (23) to allow adjustment of the generator (15) by the control device (22) based on the behavior of the plasma detected by the plasma sensor (15),
wherein the control device (22) is configured to continuously determine an adjustment of the different adjustments such that at least one of an ignition readiness and a stability of the plasma created at the electrode is just maintained, and
wherein the control device (22) is configured to operate the generator (15) during operation of the instrument (12) in a treatment phase with a voltage form that is pulsed at a medium frequency (MF) having a pulse/pause ratio after build-up of the plasma has been achieved in an ignition phase, wherein the pulse/pause ratio is reduced for the treatment phase following a subsequent ignition phase, if a stable presence of the plasma has been detected by the plasma sensor within a treatment duration in at least one treatment phase and wherein the pulse/pause ratio is increased, if an extinction tendency of the plasma has been determined.

* * * * *